United States Patent [19]
Lilja et al.

[11] Patent Number: 5,866,349
[45] Date of Patent: Feb. 2, 1999

[54] METHOD FOR DETERMINATION OF GLUCOSE IN WHOLE BLOOD AND CUVETTE AND PHOTOMETER FOR CARRYING OUT SAID METHOD

[76] Inventors: Jan Evert Lilja, Södra Brunnsvägen 63, S-253 68 Helsingborg; Sven-Erik Lennart Nilsson, Döbeliusvägen 39, S-253 67 Helsingborg, both of Sweden

[21] Appl. No.: 768,255

[22] PCT Filed: Apr. 24, 1990

[86] PCT No.: PCT/SE90/00273

§ 371 Date: Oct. 16, 1991

§ 102(e) Date: Oct. 16, 1991

[87] PCT Pub. No.: WO90/12890

PCT Pub. Date: Nov. 1, 1990

[30] Foreign Application Priority Data

Apr. 25, 1989 [SE] Sweden .................................. 8901514

[51] Int. Cl.$^6$ .................................................. C12Q 1/54
[52] U.S. Cl. .................. 435/13; 435/14; 435/26
[58] Field of Search .................. 436/14; 435/14, 435/26, 13; 422/102

[56] References Cited

U.S. PATENT DOCUMENTS

| | | | |
|---|---|---|---|
| H602 | 3/1989 | Terashima | 436/95 |
| 3,615,228 | 10/1971 | Thiegs et al. | 436/95 |
| 3,642,444 | 2/1972 | Guehler et al. | 436/95 |
| 3,964,974 | 6/1976 | Banauch et al. | 435/4 |
| 4,088,448 | 5/1978 | Lilta et al. | 422/102 |
| 4,120,755 | 10/1978 | Pierre et al. | 435/14 |
| 4,551,427 | 11/1985 | Oraeger et al. | 435/14 |
| 4,637,978 | 1/1987 | Dappen | 435/11 |
| 4,865,813 | 9/1989 | Leon | 436/165 |
| 4,990,457 | 2/1991 | Tanaka et al. | 436/70 |
| 5,112,490 | 5/1992 | Turpen | 436/178 |

OTHER PUBLICATIONS

Ohkubo et al; Clin. Chem. 27(7): 1287–1290 (1981).
Raabo; Clin. Chem. 34 (1): 173 (1988).

*Primary Examiner*—Ralph Gitomer
*Attorney, Agent, or Firm*—Kane,Dalsimer,Sullivan, Kurucz, Levy, Eisele and Richard, LLP

[57] ABSTRACT

A sample of whole blood is contacted with a reagent which by chemical reaction with glucose in the sample brings about a detectable dye concentration change (10) the size of which is determined as a measure of the glucose content of the sample. The sample is initially introduced undiluted in a microcuvette having at least one cavity for receiving the sample. The cavity is internally pretreated with the reagent in dry form, and the chemical reaction takes place in the cavity. Active components of the reagent comprise at least a hemolyzing agent for exposing glucose contained in the blood cells of the sample for allowing total glucose determination, and agents taking part in the chemical reaction and ensuring that the dye concentration change (10) takes place at least in a wavelength range (14) outside the absorption range (12) of the blood hemoglobin. An absorption measurement is performed in said wavelength range directly on the sample in the cuvette. A pretreated disposable cuvette with such a reagent and a photometer are also described.

6 Claims, 8 Drawing Sheets

METHOD FOR DETERMINATION OF GLUCOSE IN WHOLE BLOOD AND CUVETTE AND PHOTOMETER FOR CARRYING OUT SAID METHOD

The present invention relates to a method for quantitatively determining total glucose content in whole blood, and to a disposable cuvette and a photometer for carrying out the method.

Determination of whole blood glucose is made for diagnosing and controlling diabetes, and also in endocrinological investigations. In uncertain cases of unconciousness, too, determination of whole blood glucose may be justified. Diabetes is one of the world's major health problems, and it is estimated that more than 40 million people suffer from this disease and that the prevalence of type II diabetes seems to increase.

Several methods for determining glucose are known. Many old methods have today been abandoned because of unspecificity or the involvement of carcinogenic reagents.

By glucose in blood, whole blood glucose, is meant non-protein-bound glucose present in the blood. Glucose is freely distributed in the extracellular water and also in the intracellular water, e.g. in the red blood cells, but not necessarily in the same concentration. This means that the total content of glucose in whole blood differs from the total content of glucose in plasma or serum. The diagnostic criteria for e.g. diabetes are predominantly based on whole blood glucose. To the clinician, it is therefore clearly advantageous to have the glucose determinations made directly on whole blood. The difference between determinations of glucose in whole blood and glucose in plasma or serum is discussed by W. T. Caraway: Amer. J. Clin. Path. 37:445, 1962. Many glucose tests currently used, where intact red blood cells are removed, incorrectly state their results as blood glucose and may therefore cause confusion in medical diagnosis because of the different references used.

Most of today's specific glucose determination methods are based on reagents containing enzymes or enzyme systems. Three different enzyme systems are predominant, viz. glucose oxidase, hexokinase and glucose dehydrogenase (GDH).

The present invention preferably relies on reagents containing glucose dehydrogenase (GDH). Previously known determination methods using GDH are described in U.S. Pat. No. 4,120,755 and U.S. Pat. No. 3,964,974. These prior art determination methods using GDH are traditional wet-chemical methods.

None of the above-mentioned methods is however suitable for determining glucose in undiluted whole blood. Although Example 7 in U.S. Pat. No. 3,964,974 describes a whole blood glucose method, this method is based on dilution and protein precipitation or separate hemolysis of the blood sample.

EP 84112835.8 describes a whole blood glucose method for undiluted blood. The chemical enzyme reaction used is based on glucose oxidase, and an optical reflectance measurement is carried out at a wavelength above 600 nm. It is well known that hemoglobin interferes with oxidase reactions. Also, oxidase reactions require access to free oxygen. Therefore, using a microcuvette for performing a whole blood glucose determination with the glucose oxidase system in undiluted blood involves substantial problems.

From U.S. Pat. No. 4,088,448 is previously known a microcuvette which can be used for hemoglobin measurement (Hb measurement) of blood. The cuvette is pretreated with a reagent, such that when a blood sample is drawn into the cuvette, the walls of the red blood cells are dissolved and a chemical reaction is initiated, the result of which allows Hb determination by absorption measurement directly through the cuvette which, to this end, has an accurately defined gap width.

The method according to U.S. Pat. No. 4,088,448 for Hb determination on glucose is not easily applied in practice since an absorption measurement for determining the glucose content is strongly interfered with by the absorption caused by the hemoglobin. Variations in the hemoglobin concentration will therefore interfere with the glucose determination to a considerable extent.

Thus, present-day methods are complicated. They often require dilution of the blood sample or only perform a glucose determination on the blood plasma without taking into account the glucose contents of the red blood cells.

It is therefore evident that a simple, reliable and quick method for quantitatively determining the total content of glucose in undiluted whole blood would be an important aid in diagnosing and controlling diabetes.

One object of the present invention is to provide a method for quantitatively determining the total content of glucose in undiluted whole blood by transmission photometry. Another object is to provide a cuvette and a photometer for such determination.

Generally, the above-mentioned interference problem caused by the hemoglobin content is solved according to the invention in the following way:

By using a suitable reagent, it is possible first to cause the walls of the red blood cells to dissolve, and then to bring about a chemical reaction between the total glucose content of the blood sample and the reagent, which reaction yields chemical compounds which are based on the glucose and the absorption range of which, wavelengthwise, is at least partly outside the wavelength range of the hemoglobin absorption range. Thus, by absorption measurements at suitably selected wavelengths it is possible to completely eliminate the influence of the hemoglobin on the measuring result and to achieve very quick glucose determination.

Thus, the invention provides a method for glucose determination in whole blood, in which a sample of whole blood is contacted with a reagent which by chemical reaction with glucose in the sample brings about a dye concentration change which is detectable in the sample and the size of which is determined as a measure of the glucose content, the method being characterised by the steps of introducing the sample undiluted in a microcuvette having at least one cavity for receiving the sample, said cavity being internally pretreated with the reagent in dry form and said chemical reaction then taking place in said cavity, selecting as active components included in the reagent at least a hemolysing agent for exposing glucose contained in the blood cells of the sample for allowing a quantitative total glucose determination in a whole blood hemolysate, and agents participating in the chemical reaction and ensuring that the dye concentration change takes place at least in a wavelength range outside the absorption range of the blood hemoglobin, and performing an absorption measurement at said wavelength range directly on the sample in the cuvette.

Preferred embodiments of the inventive method are stated in the subclaims 2–7.

According to a preferred embodiment of the invention, the method comprises the steps of supplying undiluted whole blood to a dry reagent in a cuvette having a small gap width including a hemolysing agent, GDH, diaphorase or analog thereof, NAD or analog thereof, detergent and a dye-forming substance, and photometrically measuring the concentration of dye formed by transmission measurement in a filter photometer. Diaphorase analogs are substances having redox properties of the type phenazine mettrosulphate or phenazine ettrosulphate. These may replace diaphorase substances, but are unsuitable from the point of view of toxicity.

The glucose dehydrogenase method is specific to β-glucose. In blood, α-glucose and β-glucose exist in a temperature-dependent equilibrium. When lowering the temperature of a blood sample, the equilibrium is shifted towards a larger proportion of α-glucose. The change of equilibrium is slow. The reaction speed of the glucose dehydrogenase method is affected by the enzyme mutarotase and, thus, the α-glucose/β-glucose equilibrium. In blood glucose determination, it is essential that the analysis is carried out without any delay to prevent inherent metabolism in the sample. Since the spontaneous α-β reaction occurs very slowly and the body temperature is sufficiently constant for ensuring the α/β equilibrium, mutarotase can advantageously be excluded in the case of direct testing on body-temperature blood, yet allowing calibration of the photometer in total glucose. In addition to the cost reduction, the advantages of the method reside in a decreased reaction time and an extended analytical range. A disadvantage is that calibration and control solutions should be brought to proper temperature during at least 1 h.

According to a preferred embodiment of the invention, a reagent system of the glucose dehydrogenase type consists of a hemolysing agent for breaking up the red blood cells and liberating hemoglobin, GDH diaphorase or analog to make the NADH reaction visible, NAD or analog, detergent or a dye-forming substance, e.g. taken from the group of tetrazolium compounds. In addition to these active substances, other chemical substances can be used as production aids.

The absorbance by the hemoglobin liberated during hemolysis is described in E. J. van Kampen and W. G. Zijlstra (1965): "Determination of hemoglobin and its derivations" in Adv. Clin. Chem. 8, 141–187, p 165, FIG. 12. It is seen from this figure that in case an absorption measurement occurs at a wavelength above 645 nm, the effect of any hemoglobin derivative is minimised.

Another type of interference in absorption measurements is e.g. particle scattering of the light from cells, fat, dust or other deficiencies. By measuring at another wavelength, often above the primary measuring wavelength, here neither hemoglobin nor the dye formed gives rise to any interfering absorbance, this background absorbance can be compensated for.

The reaction process of the glucose dehydrogenase system is well known and described in U.S. Pat. No. 3,964,974. This publication reports on a reaction process comprising tetrazolium salt with absorption in the visible range.

An essential feature of the method according to the invention is the use of a glucose dehydrogenase reaction proceeding to end-point, both chemically and in respect of absorption photometry. In terms of safety and reliability, such a reaction is preferable to the user.

Optical methods for quantitative determination of the concentration of a chemical substance in a solution are well known and well documented. Absorption photometry is an optical determination technique. The theory behind absorption photometry and the design of a photometer are described in Skoog and West: "Fundamentals of Analytical Chemistry", Section Edition, Chapter 29. Basically, a photometer consists of three parts, an optical part, a mechanical part and an electronic part. The optical part consists of a light source with a monochromator or interference filter and a light detector, and in some cases a lens system. The mechanical part comprises the suspension of the optical part and means for transporting cuvettes with chemical solution. The electronic part is designed for the control and monitoring of the light source and the measuring signals from light detectors, these signals being so processed that the user can read a numerical value which is related to or represents the chemical concentration measured.

Such a photometer construction is disclosed in U.S. Pat. No. 4,357,105. This patent describes a photometer for determining hemoglobin in blood, which provides optimisation with known components, such that the photometric determination occurs as close to the measuring wavelength 540 nm as possible. The adjustment to the measuring wavelength 540 nm is carried out by using a light emitting diode and a light filter of the didymium-oxide glass type. In an alternative embodiment, a light emitting diode is used within the infrared range for measuring turbidity in the chemical solution. This known photometer is intended to be used for ordinary wet-chemical hemoglobin determination methods, having a degree of dilution of 1/200 and above between blood and reagent.

A photometer for determining the glucose content in whole blood according to the method described, i.e. supplying dry glucose reagent to undiluted blood and performing a photometric two-wavelength measurement on a microcuvette, must be simple, reliable and available at a low cost. Since the cuvette contains a dry glucose reagent, it is of the disposable type, and the transport of the cuvette, after filling with undiluted blood, must be uncomplicated and minimise the effect of stray light. In terms of operation, the photometer must be photometrically stable and require a minimum of controlling.

Thus, in order to carry out the inventive method the invention further provides a disposable cuvette according to claim 8 pretreated with a dry reagent, and a photometer according to claim 9 operating at two separate wavelengths, preferred embodiments of the latter being stated in claims 10 and 11.

A photometer for carrying out the inventive method for measuring whole blood glucose in small volumes in undiluted blood by means of a microprocessor for monitoring and controlling and having arithmetic calculation capacity, as well as light emitting diodes provided with an interference filter, gives a construction which is easy to handle, technically stable and employs silicon electronics throughout, has low power consumption, is highly reliable and can be manufactured at a low cost. If the mechanical part, the outer casing and the bottom as well as the cuvette transport means, including the part where the optical components are attached, is made of injection-moulded plastic, the overall production costs for the photometer will be low.

A microprocessor-assisted photometer is able to control all processes and carry out all calculations including logarithmic transformations. The light emitting diodes of a photometer for two-wavelength measurements are pulsed via the microprocessor such that only one light emitting diode is lit at a time. Light emitting diodes are highly advantageous by having no afterglow. In order to ensure that the light emitting diodes do not lose their light intensity by ageing, the photometer is designed such that maximal light intensity, corresponding to 100% light, is regularly measured between different cuvette measurements. By designing the mechanical cuvette transport function such that the photometer can sense if a cuvette should be measured or if the total intensity, 100% light, should be measured, the photometer can operate with a compensation for light intensity. By the possibility of establishing whether the measured value is a cuvette value or a blank value, 100% transmission, the photometer can operate, by means of its microprocessor equipment, without any logarithmic analog amplifiers. The absence of logarithmic analog amplifiers increases the reliability and the stability of the photometer while at the same time arbitrary accuracy in the logarithmic operation is achieved by a logarithmic algorithm in the microprocessor program. A further advantage of a microprocessor-assisted photometer is that different forms of arithmetic curve adaptations of calibration curves or linearisations can easily be introduced in the program. By the microprocessor function, it is also possible to use different forms of end-point routines, i.e. the program can itself decide when the end-point has been reached, which can be done with different accuracies for different concentration levels, where so desirable.

The invention will now be described in more detail with reference to the accompanying drawings.

Figure 1:
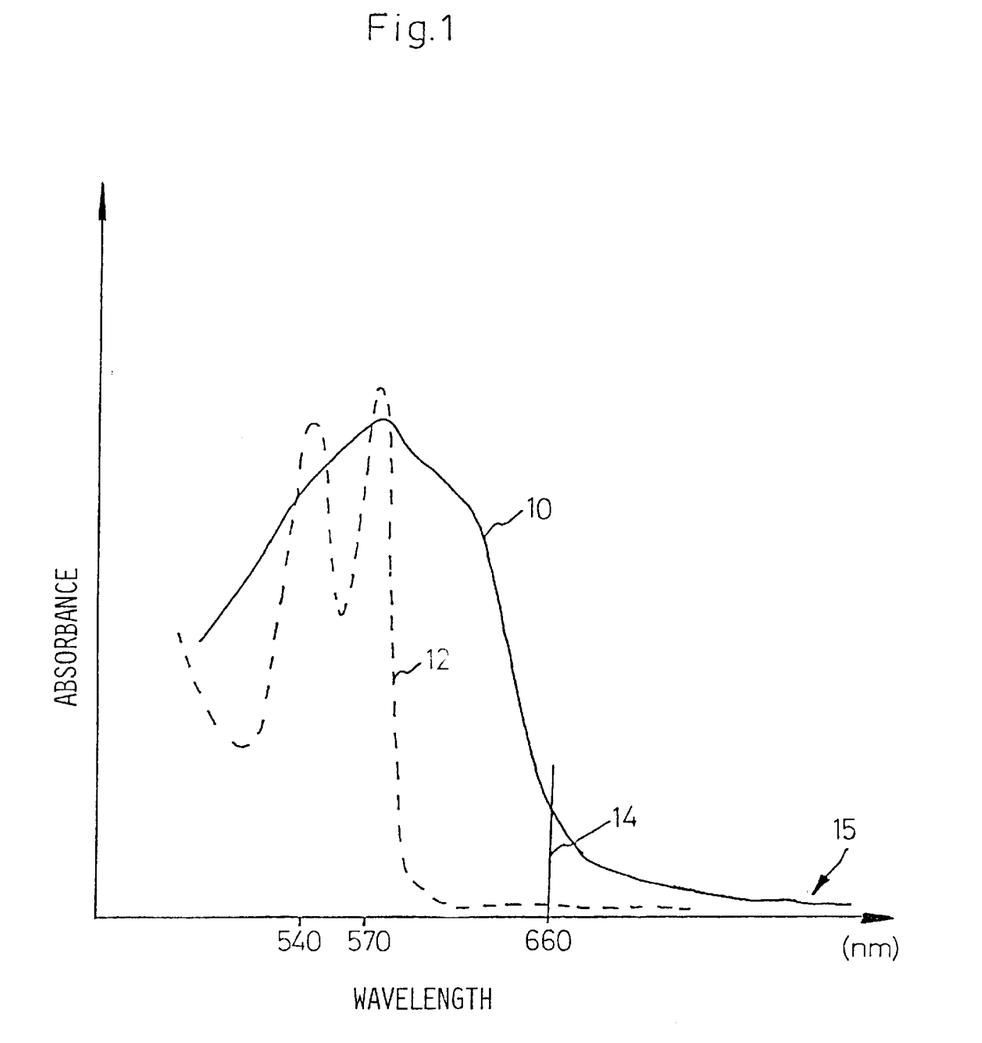
FIG. 1 is a graph with absorbance set against wavelength, both for a mix of hemoglobin derivatives and for a dye-forming substance included in a glucose reagent.

FIG. 1 indicates by a full line 10 an absorption spectrum for a tetrazolium salt, 3-(4,5-dimethyl thiazolyl-1-2)-2,5-diphenyl tetrazolium bromide (MTT), and by a dashed line 12 an absorption spectrum for hemolysed blood. It Is seen that above 600 nm there is a wavelength range where MTT can be quantitatively determined with a minimum of interference by hemoglobin. It also appears that compensation for background interference can occur at higher wavelengths. At two-wavelength measurements in absorption, it is essential to use wavelengths which are distinctly separated so as not to interfere with each other. The interference filters used in the filter photometer are defined wavelengthwise by the wavelength where maximal light transmission is obtained. In addition, an interference filter has a half bandwidth defined where a maximum of 50% of the light transmission is obtained.

FIGS. 2A, 3A, 4A and 2B, 3B, 4B show different embodiments of a microprocessor-assisted photometer. Version 'A' in these Figures shows a photometer without a logarithmic amplifier, the logarithmic operation taking place in the program of the microprocessor. Version 'B' in these Figures makes use of a separate logarithmic amplifier 19. The use of a separate logarithmic amplifier 19 means simpler programs in the microprocessor, but poorer technical characteristics of the photometer.

Figure 2A:
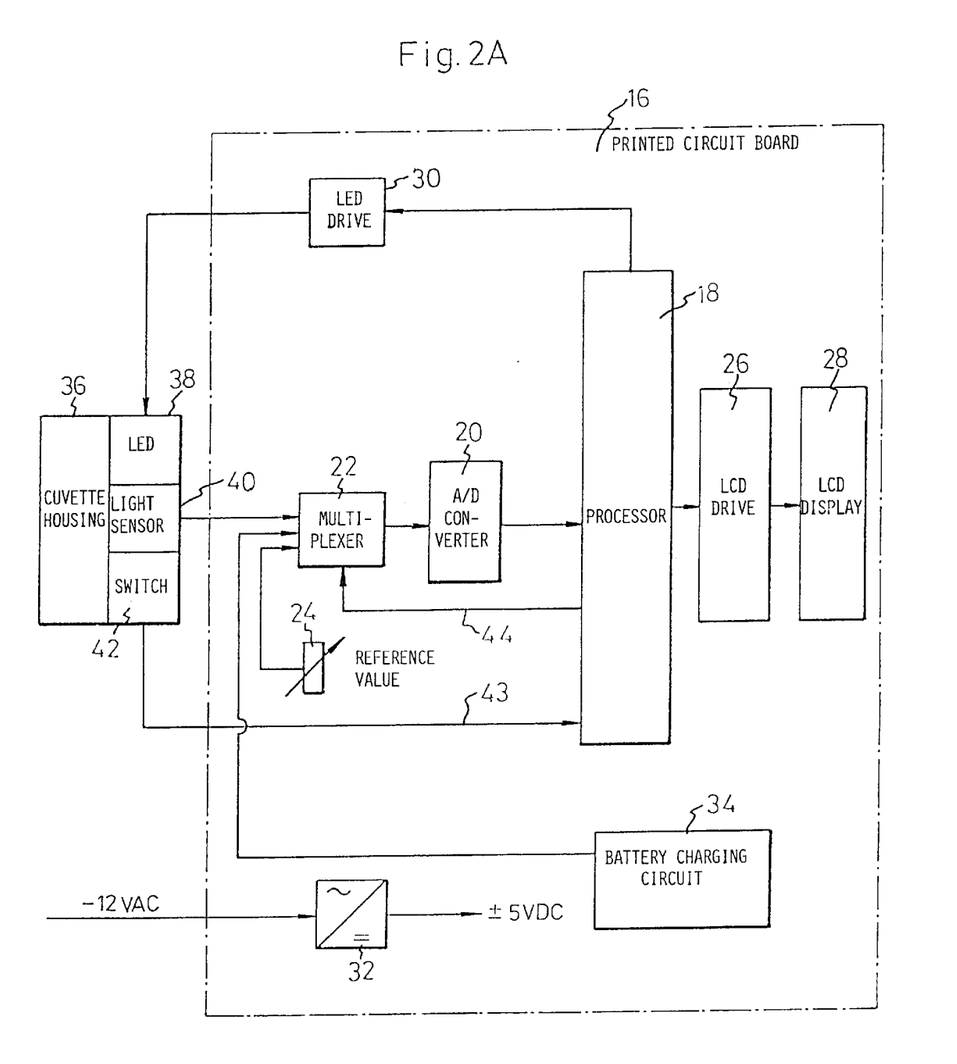
FIGS. 2A, 3A and 4A show three different embodiments of an inventive photometer.
Figure 2B:
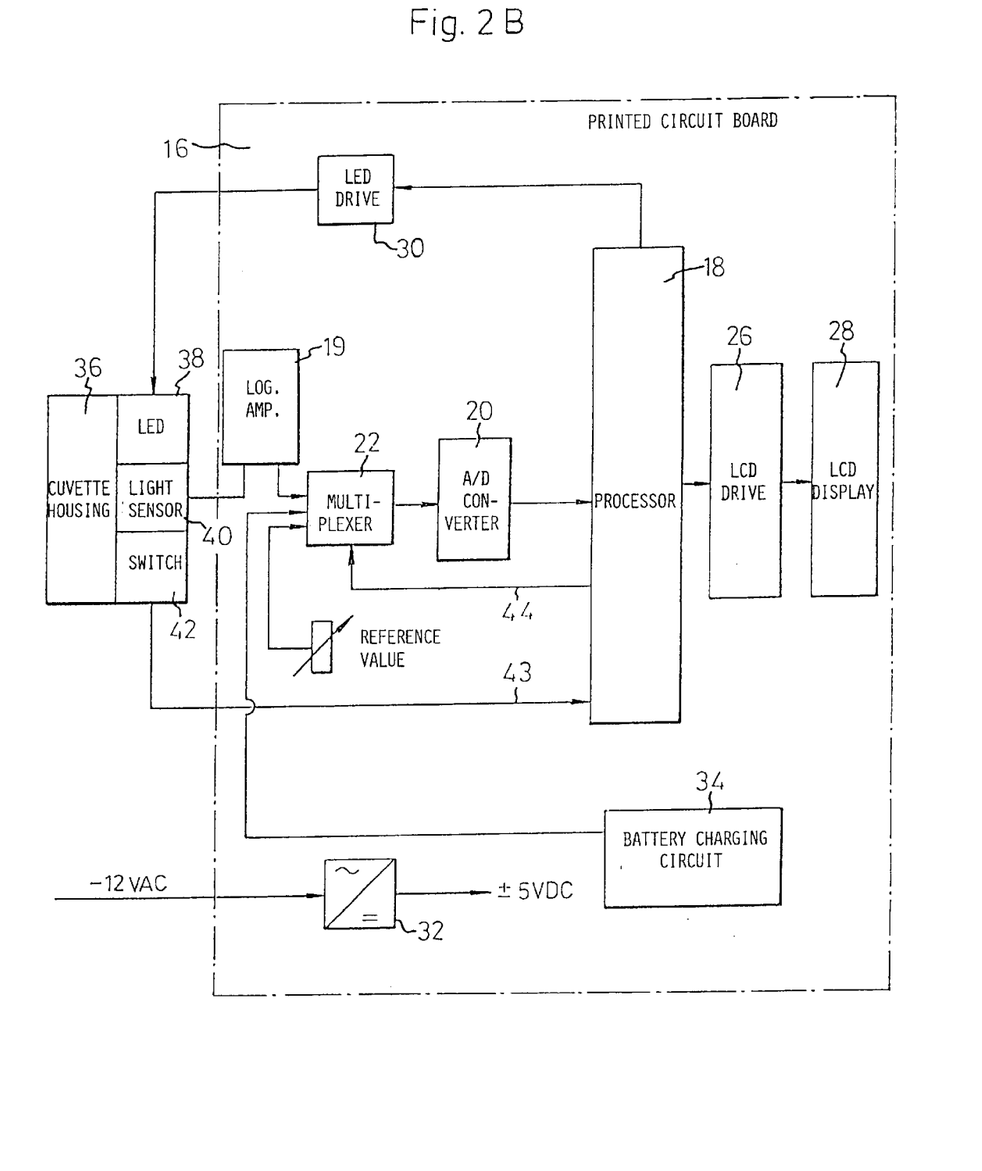
FIGS. 2B, 3B and 4B correspond to the embodiments of FIGS. 2A, 3A and 4A, respectively, but include a separate logarithmic amplifier.
Figure 3A:
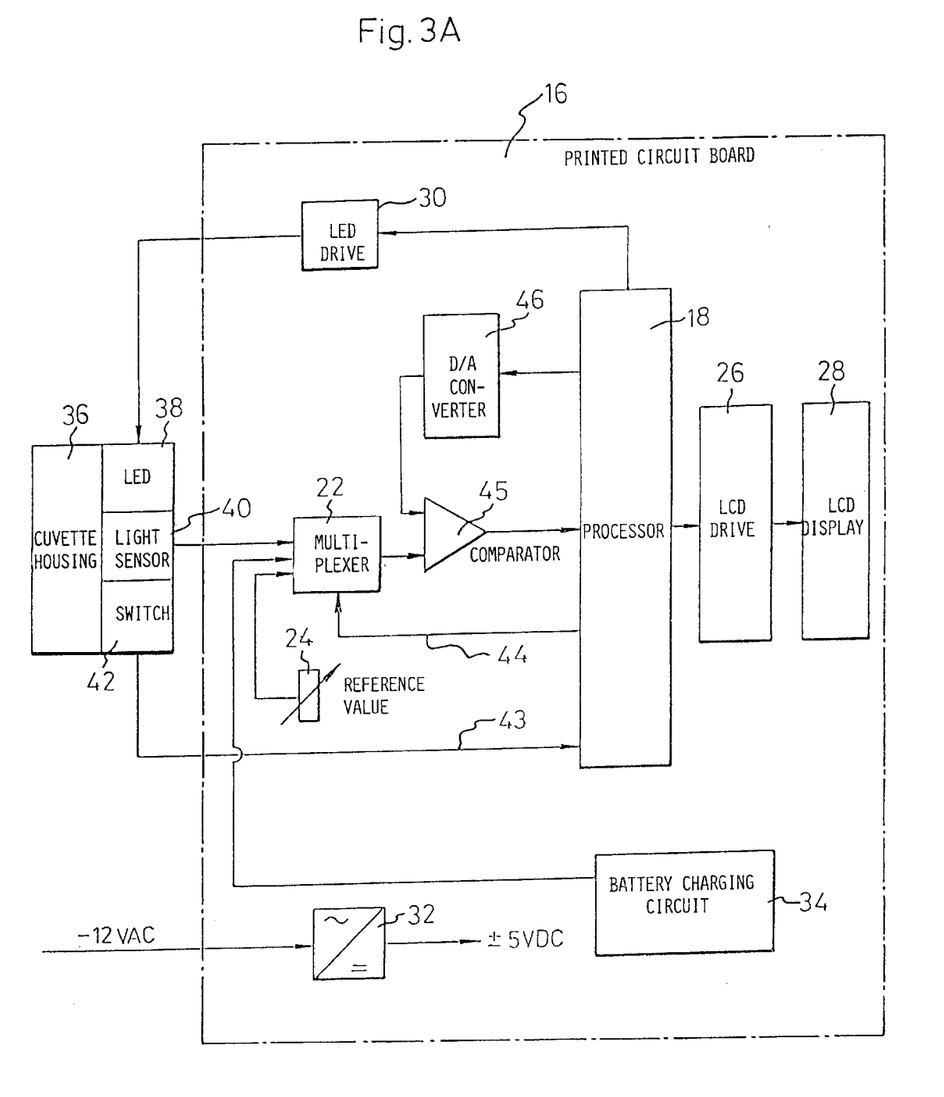
Figure 3B:
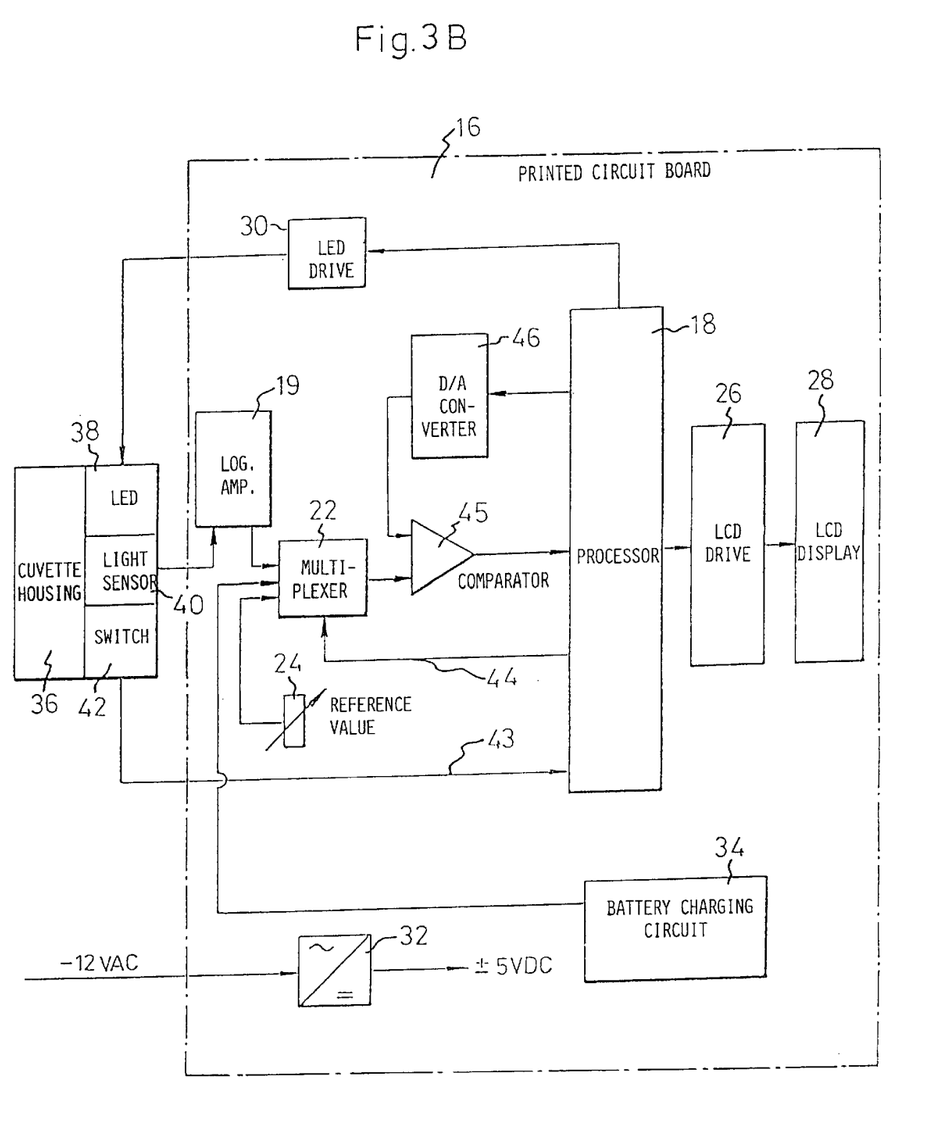

FIGS. 2A, 2B and 3A, 3B differ in that FIGS. 3A, 3B make use of a digital-to-analog converter 46 when passing from analog to digital form. This arrangement has the advantage of being economical, but gives poorer stability by necessitating peripheral equipment.

Figure 4A:
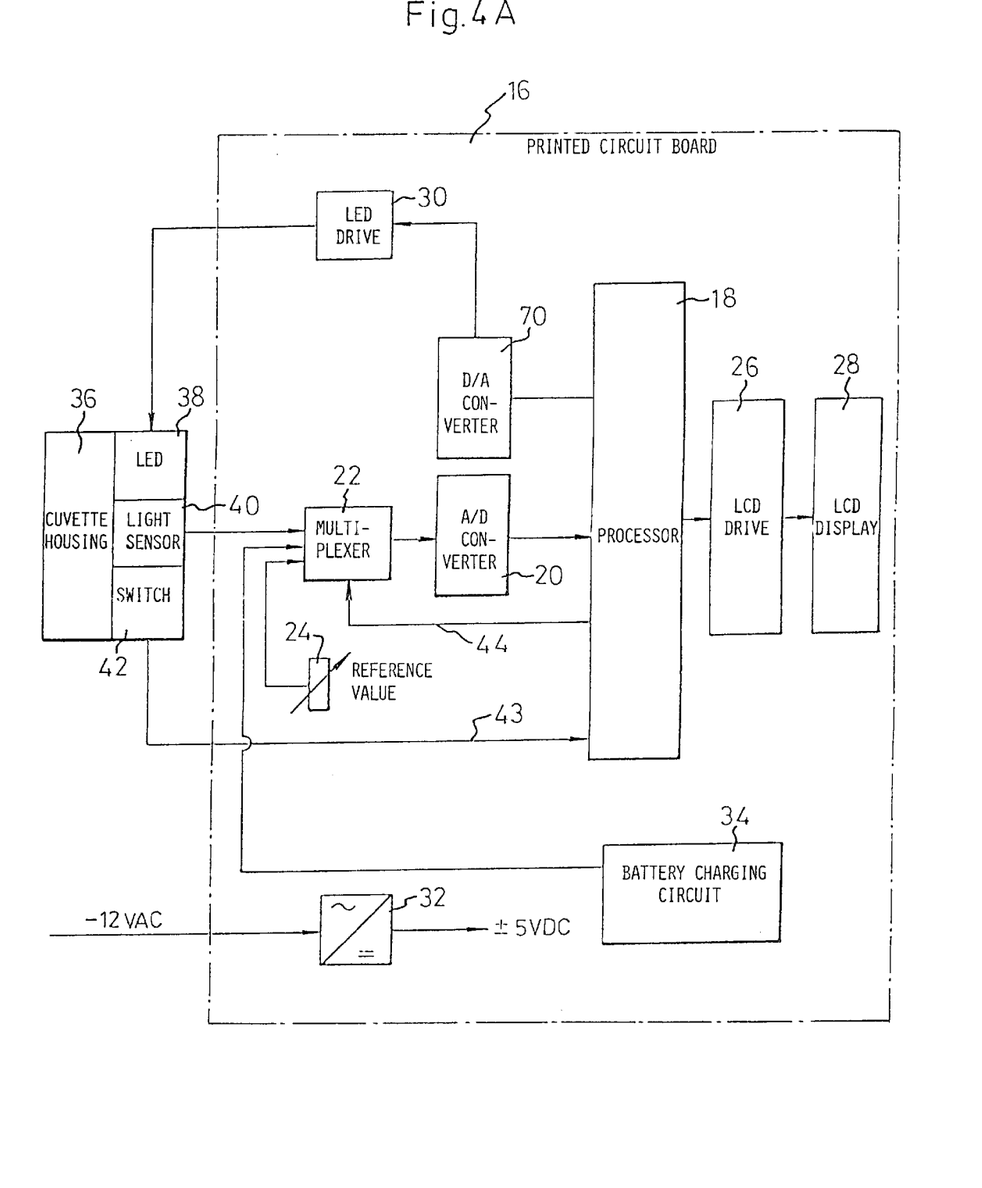
Figure 4B:
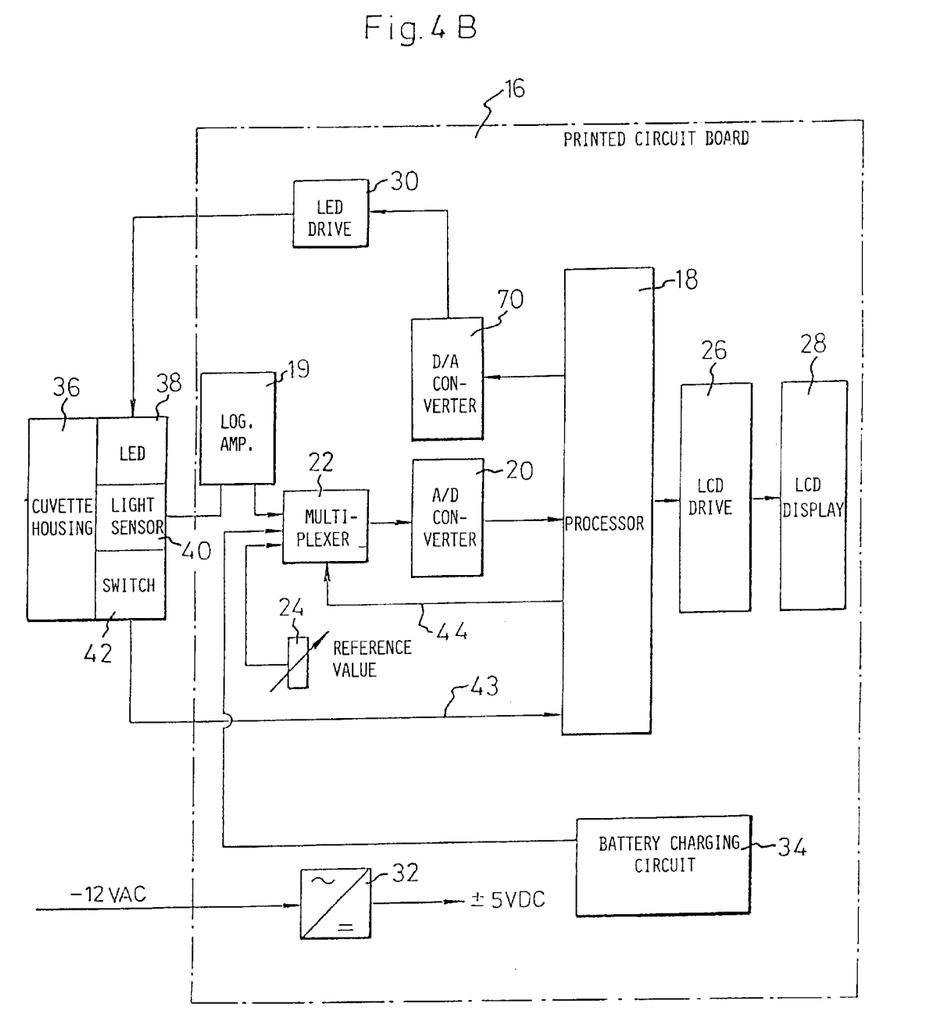

The photometer in FIGS. 2–4 physically consists of two structural blocks: one optical housing and one electronic printed circuit board 16. The electronic printed circuit board is of standard type where the components used are applied by surface mounting or soldering in traditional manner in a drilled laminate board. In certain cases, it is possible to use a printed circuit board allowing a combination of different mounting techniques.

The embodiment in FIG. 2A will now be described in more detail. A printed circuit board 16 included in the photometer is schematically shown by dash-dot lines and contains a microprocessor 18, an analog-to-digital converter 20, a multiplexer 22, a potentiometer 24, an LCD drive unit 26, an LCD display unit 28, a light emitting diode drive circuit 30, a mains rectifier 32, a battery charging circuit 34, and peripheral equipment (not shown) of a type known to a person skilled in the art.

The printed circuit board 16 is connected to the other photometer part comprising a cuvette housing 36, two light emitting diodes 38, a light sensor 40, and a switch 42.

In operation, the multiplexer 22 receives analog signals from the light sensor 40, from the battery charging circuit 34 and from the potentiometer 24 and transmits, in accordance with control instructions 44 from the microprocessor 18, one of these signals to the analog-to-digital converter 20. This converts the signal to a form which can be handled by the processor 18 which depending on the signal received executes different operations.

The processor 18 receives the signal from the potentiometer 24, which is adjustable by the user, when the photometer is calibrated by means of a sample of known glucose content. In this way, a constant is established in the algorithm by means of which the glucose content is calculated on the basis of the transmittance measured.

The processor 18 receives the signal from the battery charging circuit 34 when the processor 18 should compensate for varying battery charge.

The processor 18 receives the digitilised measuring signal from the light sensor 40, both when measuring 100% transmittance as reference, and when measuring transmittance through the blood sample in a disposable cuvette placed between the light emitting diodes 38 and the light sensor 40.

On the basis of a preprogrammed algorithm, the processor 18 calculates the glucose content of the sample and emits the result to the LCD drive circuit 26 for displaying it to the user on the LCD display 28.

In FIGS. 2B, 3A and 3B as well as 4A and 4B, like parts, as in FIG. 2A, are represented by like reference numerals.

In the variant of FIG. 3A, the analog-to-digital converter in FIG. 2A is excluded and replaced by a combination of a comparator 45, a digital-to-analog converter 46 and the microprocessor 18. The processor 18 emits to the converter 46 a digital value which is converted to analog form and which is successively changed by the processor 18 until a zero signal is obtained on the output of the comparator 55. Otherwise, the function is the same as in FIG. 2A.

Figure 5:
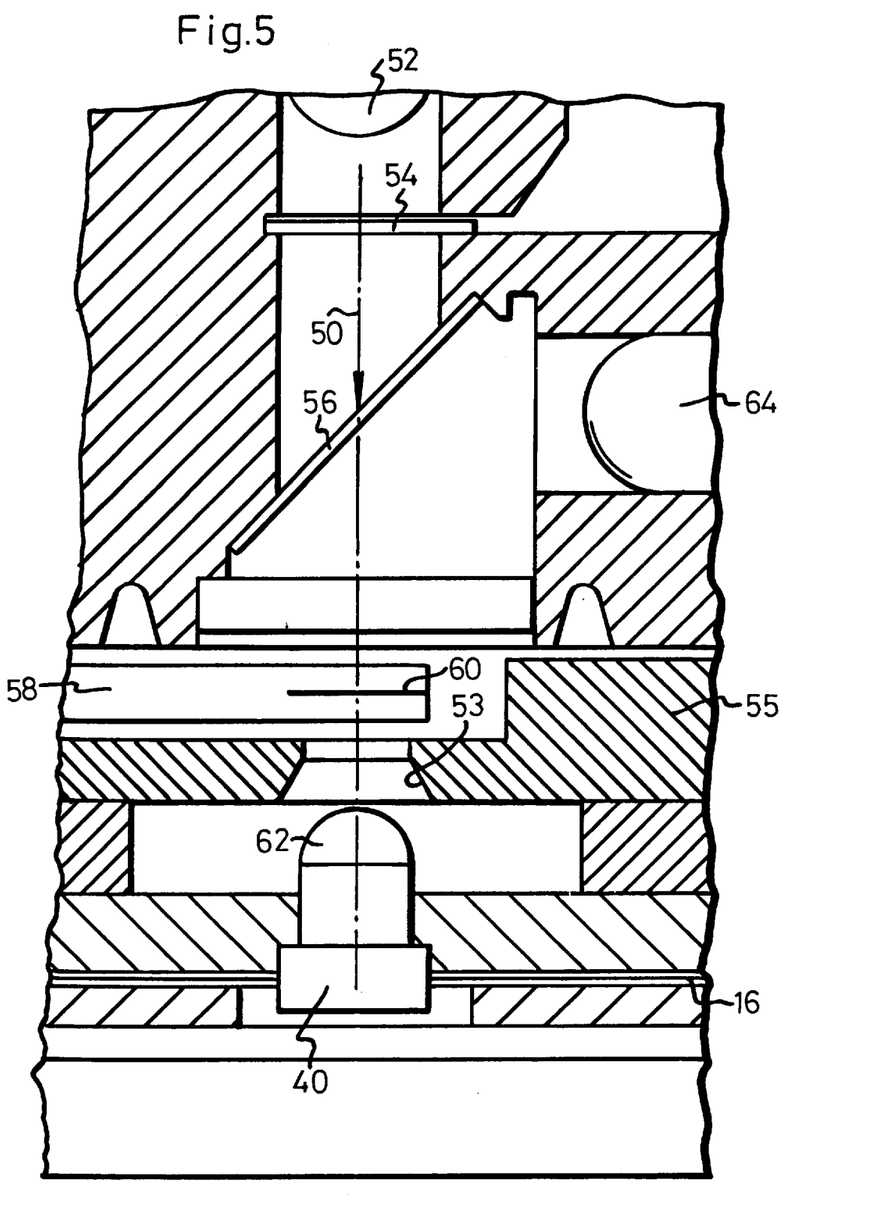
FIG. 5 schematically shows a broken-apart section of an embodiment of the optical part of an inventive photometer.

The basic design of the optical housing appears from FIG. 5. The arrangement comprises two light emitting diodes 52, 64 disposed at 90° to each other. To obtain a similar optical axis, the light emitting diodes should be adjusted prior to mounting.

A photometer for glucose in undiluted blood can have its measuring wavelength at 660 nm (at 14 in FIG. 1). As a result of the measurement of the absorbance flank on the dye formed, the half bandwidth of the measuring wavelength must be well defined. The background wavelength for measuring glucose in undiluted blood should be above 700 nm. A suitable choice of background wavelength is where commercial light emitting diodes are available, e.g. 740–940 nm.

In FIG. 5, it is seen how a light ray 50 from a red light emitting diode 52 passes an interference filter 54 having maximal light transmission at 660 nm and a half bandwidth less than 15 nm, and through a mirror disposed at an angle of 45°. After the light ray 50 has passed the interference filter 54 and the mirror 56, it passes through the cavity 60 of the cuvette 58, which cavity contains undiluted whole blood and glucose reagent or glucose reagent products, and reaches the light detector 40 through an opening 53 in a cuvette holder 55. The light detector 40 can be provided with a small collecting lens 62.

The light ray from the infrared light emitting diode 64 is reflected on the rear side of the 45°-inclined mirror 56, passes through the cavity 60 of the cuvette 58 and reaches the detector 40. The infrared background wavelength is measured with the second light emitting diode 64 and on a plane absorbance level (e.g. at 15 in FIG. 1), the half bandwidth of the infrared light emitting diode 64 being of little importance.

If the cuvette transport device 55, e.g. a carriage construction, is equipped with an element that can be sensed by a stationarily arranged sensor, the microprocessor 18 can easily be supplied with information 43 about the position in which the cuvette 58 is situated. If a carriage 55 is used as cuvette conveyor, it may have a magnet which is sensed by two fixed magnetic reed relays. When the carriage is in the extracted position for introducing the cuvette 58, maximal light, 100% light, is measured.

Maximal light is measured for both measuring wavelength and background measuring wavelength. By continuously calculating the quotient in percent between measuring value, cuvette in measuring position and maximal light, good compensation for ageing phenomena in the light sources 52, 64 is obtained in transmittance measurement. A logarithmic operation on the transmission value is executed in the microprocessor 18, or in a separate circuit (see version 'B') for receiving a measure of absorbance.

The current of the light detector 40 reaches an operational amplifier which converts current to voltage to permit easy processing of the signals on the printed circuit board 16. The microprocessor 18 also monitors whether the dark current from the detector 40 is low and compensates for the influence of the dark current by taking this into account in the calculation formulae used.

In FIGS. 2–4, there is only one movable part, viz. the potentiometer 24. The potentiometer 24 is the only component which the user can operate on the printed circuit board 16. The potentiometer 24 is used for calibrating the photometer against blood of known glucose content. To achieve maximal stability, the other components of the photometer are preferably stationary.

For economic reasons, the microprocessor is a one-chip processor. To save energy, the digit displays are of the LCD type and the photometer is supplied with energy from a mains transformer or a battery.

FIG. 4A shows another embodiment of the invention. This version uses the programming possibilities of the microprocessor 18 for providing a photometer which is easier to trim and has enhanced stability. This is achieved in that the supply of current to the two light emitting diodes 38 is controlled through a digital-to-analog converter 70 which, in terms of programming, is in feedback with the measuring signal. It is then possible, in terms of measurement, to maintain the blank value, 100% transmission, on a constant level. This constant level is electronically determined by the resolution (number of bits) in the digital-to-analog conversion.

EXAMPLE

A microcuvette 58 of the type described in the above-mentioned U.S. Pat. No. 4,088,448 was provided by freeze-drying with a dry reagent for quantitative determination of total glucose in whole blood. The microcuvette was charged with dry reagent by producing, in a first step, a water-soluble reagent composition. The water-soluble glucose reagent composition consisted of (volume 1 ml):

100 units GDH, glucose dehydrogenase
20 units diaphorase
20 $\mu$mol NAD
30 $\mu$mol MTT
25 mg White Saponin
1 ml water subjected to ion-exchange In step 2, the microcuvette was filled with about 5 $\mu$l reagent composition solution, the distance between the walls in the sample-absorbing cavity 60, which also serves as analysing cavity, being about 0.14 mm.

In step 3, the microcuvette was freeze-dried. After step 3, the microcuvette contained a dry reagent for determination of glucose in undiluted blood uniformly distributed in the cavity 60. The microcuvette was then ready for analysing.

A photometer of the type described above and equipped with a microprocessor 18 of the Intel 8751 type was provided with a suitable program for determining glucose in whole blood. The photometer was programmed in order, at end-point, to give results on glucose in whole blood expressed in mmol/l. The light emitting diodes 38 were pulsed every 15 seconds, and the light emitting diode was lit for 5 ms.

The Table below indicates the results obtained from whole blood "spiked" with glucose for achieving different glucose levels. The reference method used was a glucose dehydrogenase test system, from Merck, Gluc-DH-method, type 13886, 13887. In the reference method, spectrophotometry was performed in the UV range, i.e. at about 340 nm according to the packing specification accompanying the Gluc-DH-method. The reference method is an analytical method of the wet-chemical type.

The glucose content of the "spiked" blood samples was determined by the reference method in triplicate. On each glucose level, 10 pretreated microcuvettes were filled with undiluted blood and analysed according to the invention at the measuring wavelength 660 nm and the background wavelength 880 nm. The results obtained are indicated in the Table below.

| Method according to the invention | | |
| --- | --- | --- |
| Level mmol/l | CV % | Time to end-point (s) |
| 3.8 | 3.3 | 53 |
| 6.1 | 2.5 | 71 |
| 8.6 | 2.4 | 77 |
| 13.0 | 2.0 | 99 |
| 17.7 | 1.5 | 119 |
| 21.8 | 1.5 | 145 |

CV = Coefficient of Variation

We claim:

1. A method for determining the glucose content in whole blood, in which a sample of undiluted whole blood is contacted with a dye-containing reagent system which undergoes chemical reaction with the glucose in the whole blood sample, the method consisting essentially of the steps of:

introducing the undiluted whole blood sample in a microcuvette having at least one cavity for receiving the sample, said cavity being internally pretreated with the reagent in a dry form and said chemical reaction then taking place in said cavity, the reagent being comprised of a hemolyzing agent and agents used in the glucose dehydrogenase method, said agents being comprised of glucose dehydrogenase and a redox indicator dye, the hemolyzing agent exposing the glucose contained in the blood cells of the whole blood sample permitting a quantitative total glucose determination in a whole blood hemolysate, the agents which participate in the chemical reaction ensure that a dye concentration change takes place in a wavelength range above 650 nm and, performing an absorption measurement at said wavelength range directly on the sample in the cuvette, and further conducting a secondary absorption measurement to compensate for background interference in a wavelength range above 700 nm.

2. The method as claimed in claim 1, wherein the reagent is further comprised of diaphorase.

3. The method as claimed in claim 2 wherein the reagent is further comprised of mutarotase.

4. The method as claimed in claim 1 wherein said chemical reaction is an end-point reaction, said absorption measurement being carried out only when said dye concentration change is substantially terminated.

5. A disposable cuvette for carrying out a determination of the glucose content of undiluted whole blood where a sample of undiluted whole blood is contacted with a dye-containing reagent system undergoes chemical reaction with the glucose in the undiluted whole blood sample, the cuvette being comprised of at least one cavity for receiving the undiluted whole blood sample, said cavity being internally pretreated with a reagent in dry form and said chemical reaction occurring in said cavity after introduction of the sample in undiluted form, the reagent being comprised of a hemolyzing agent and agents used in the glucose dehydrogenase method, said agents being comprised of glucose dehydrogenase and a redox indicator dye, the hemolyzing agent exposing the glucose contained in the blood cells of the whole blood sample permitting a quantitative total glucose determination in a whole blood hemolysate, the agents which participate in the chemical reaction ensure that the dye concentration change takes place in a wavelength range above 650 nm and that the cuvette is at least partly transparent for permitting an absorption measurement directly on the sample in the cavity of the cuvette in said wavelength range.

6. A method for determining the glucose content in undiluted whole blood, in which a sample of undiluted whole blood is contacted with a reagent which by chemical reaction with glucose in the undiluted whole blood sample brings about a dye concentration change which is detectable in the sample, whereby the size of the dye concentration change is used to determine the measure of the glucose content, the method consisting essentially of the steps of:

introducing a sample of undiluted whole blood in a microcuvette having at least one cavity for receiving the sample, said cavity being internally pretreated with a reagent in dry form and said chemical reaction with the glucose in the sample taking place in said cavity, the reagent being comprised of a hemolyzing agent for exposing glucose contained in the blood cells of the sample for allowing a quantitative total glucose determination in a whole blood hemolysate, glucose dehydrogenase, NAD or analog thereof, diaphorase or analog thereof, and a dye, the dye undergoing a concentration change upon said chemical reaction with the reagent corresponding to the blood glucose content of the sample, determining by transmission photometry the concentration change of the dye at a wavelength that is in an absorption range above 650 nm., the dye being selected so that the dye concentration change takes place at least in a wavelength range above 650 nm. which is outside the absorption range of the blood hemoglobin, and further conducting a secondary absorption measurement to compensate for background interference in a wavelength range above 700 nm.

* * * * *